United States Patent [19]

Perilstein

[11] 3,975,279

[45] Aug. 17, 1976

[54] HYDRAULIC FLUID COMPOSITIONS

[75] Inventor: Warren L. Perilstein, Orchard Lake, Mich.

[73] Assignee: Ethyl Corporation, Richmond, Va.

[22] Filed: Nov. 24, 1975

[21] Appl. No.: 634,869

[52] U.S. Cl. .............................. 252/78.5; 252/46.7; 252/52 R; 252/407
[51] Int. Cl.$^2$ .................. C09K 50/00; C10M 1/48; C10M 3/42; C09K 15/06
[58] Field of Search ................ 252/46.7, 52 R, 78, 252/407

[56] References Cited
UNITED STATES PATENTS

| | | | |
|---|---|---|---|
| 3,182,023 | 5/1965 | Plemich et al. | 252/46.7 |
| 3,346,668 | 10/1967 | Dalton et al. | 252/78 |
| 3,383,318 | 5/1968 | McHugh et al. | 252/78 |
| 3,553,131 | 1/1971 | Hepplewhite et al. | 252/46.7 |
| 3,932,290 | 1/1976 | Koch et al. | 252/78 |

Primary Examiner—Delbert E. Gantz
Assistant Examiner—I. Vaughn
Attorney, Agent, or Firm—Donald L. Johnson; John F. Sieberth; Robert A. Linn

[57] ABSTRACT

$\beta$-(Halpropyl)-thionophosphates are stabilized by styrene oxides. The styrene oxide stabilized $\beta$-(halopropyl)-thionophosphates are added to hydraulic fluid to enhance antiwear and extreme pressure properties of the hydraulic fluid.

15 Claims, No Drawings

HYDRAULIC FLUID COMPOSITIONS

BACKGROUND OF THE INVENTION

Unstabilized β-halopropyl esters of thionophosphoric acids are well known in the art. Their manufacture is disclosed in U.S. Pat. Nos. 2,866,805 and 2,984,681. Their use in gasoline as ignition control agents is disclosed in U.S. Pat. No. 2,862,950. The addition of these esters of thionophosphoric acids to crankcase lubricants is disclosed in DeWitt, U.S. Pat. No. 2,912,381.

The addition of various additives to base stocks of hydraulic fluids to modify certain properties of these base stocks is known in the prior art. For example, the various additives, as well as the base stocks, are described in R. E. Hatton, *Introduction to Hydraulic Fluids*, Reinhold Publishing Corporation, New York, N.Y.

SUMMARY OF THE INVENTION

According to the present invention new stabilized compositions of matter containing (1) β-(halopropyl)-thionophosphates having from 1 to 4 sulfur atoms per molecule, the halogen atom of said thionophosphate having an atomic weight of at least 35, and (2) a small but effective amount of a stabilizer selected from compounds having the formula

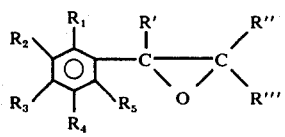

wherein $R_1$–$R_5$ and $R'$ – $R'''$ are independently selected from hydrogen and hydrocarbyl radicals, are provided.

This invention also pertains to hydraulic fluid, preferably petroleum based hydraulic fluid, and more preferably mineral oil based hydraulic fluid, stabilized additive compositions comprising the β-(halopropyl)-thionophosphates and styrene oxides of formula I which enhance the antiwear and extreme pressure characteristics of said hydraulic fluid.

Also according to the present invention improved hydraulic fluid, preferably petroleum based hydraulic fluid, and more preferably mineral oil based hydraulic fluid, compositions containing β-(halopropyl)-thionophosphates stabilized by styrene oxides of formula I are provided.

DESCRIPTION OF PREFERRED EMBODIMENTS

One embodiment of this invention pertains to stabilization of β-(halopropyl)esters of thionophosphoric acids, the halogen atoms being chlorine, bromine and/or iodine, by styrene oxides of formula I. The stabilized compounds of this invention are β-halopropyl esters of four thionophosphoric acids, namely thionophosphoric acid $(HO)_3P=S$, monothiophosphoric acid $(HO)_2(HS)P=S$, dithiothionophosphoric acid $(HO)(HS)_2P=S$, and thiothionophosphoric acid $(HS)_3P=S$.

Illustrative examples of these esters include tri-(β-chloroisopropyl)-thionophosphate, tri-(β-bromopropyl)-thionophosphate, tri-(β-iodiisopropyl)-thionophosphate, di-(β-chloroisopropyl)-(β-bromoisopropyl)-thionophosphate, di-(β-bromopropyl)-(β-chloropropyl)-thionophosphate, di-(β-chloropropyl)-(β-iodopropyl)-thionophosphate, tri-(β-chloropropyl)-monothiothionophosphate, tri-(β-bromoisopropyl)-monothiothionophosphate, tri-(β-iodopropyl)-monothiothionophosphate, O,O-di-(β-chloroisopropyl)-(β-bromopropyl)-monothiothionophosphate, O,O-di-(β-chloropropyl)-(β-iodopropyl)-monothiothionophosphate, tri-(β-chloropropyl-dithiothionophosphate, tri-(β-bromopropyl)-dithiothionophosphate, tri-(β-iodopropyl)-dithiothionophosphate, S,S-di-(β-chloropropyl)-(β-bromoisopropyl)-dithiothionophosphate, O,S-di-(β-bromopropyl)-(β-iodopropyl)-dithiothionophosphate, tri-(β-chloroisopropyl)-trithiothionophosphate, tri-(β-bromoisopropyl)-trithiothionophosphate, tri-(β-iodopropyl)-trithiothionophosphate, di-(β-chloropropyl)-(β-bromopropyl)-trithiothionophosphate, and the like.

These compounds can be prepared by two general methods. The first involves reacting at about 30°C. a thiophosphoryl trihalide, such as thiophosphoryl trichloride with a β-halopropanol, β-halopropyl thiol or a mixture of such compounds, the halogen atoms of the reactants having atomic weights of at least 35. In this method approximately 3 moles of alcohol or thiol are reacted with each mole of phosphorus reagent employed. Since 3 moles of hydrogen halide are produced, it is preferable to employ a halogen acceptor, such as an amine.

The second method for preparing these compounds involves reacting propylene oxide or propylene sulfide at about 35°C. with a phosphorus trihalide whereby a tri-(β-halopropyl)-phosphite is formed. Three moles of propylene oxide or propylene sulfide or mixtures thereof are consumed per each mole of phosphorus reagent present. The phosphite can then be reacted with elemental sulfur to produce these compounds. If desired, the propylene oxide or propylene sulfide or mixtures of the two can be reacted directly with such compounds as thiophosphoryl trichloride, thiophosphoryl tribromide, thiophosphoryl triiodide or appropriate mixtures of these reagents.

Another embodiment of the present invention pertains to the addition of these styrene oxide stabilized β-(halopropyl)-thionophosphates to hydraulic fluids, particularly to mineral oil based hydraulic fluids, to improve the lubricating and extreme wear characteristics thereof. The preferred compound of this embodiment is stabilized tri-(β-chloropropyl)-thionophosphate. There are four isomers of this compound which give excellent results when used individually. Similarly, mixtures of two or more of these isomers are eminently suited for use according to this invention. The individual isomers are tri-(β-chloro-n-propyl)-thionophosphate having the formula

di-(β-chloro-n-propyl)-(β-chloroisopropyl)-thionophosphate having the formula

-continued

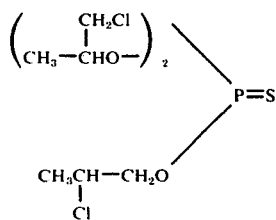

di-(β-chloroisopropyl)-(β-chloro-n-propyl)-thionophosphate having the formula

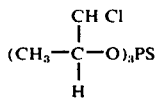

and tri-(β-chloroisopropyl)-thionophosphate having the formula $$(CH_3-\underset{H}{\underset{|}{\overset{CH\,Cl}{\overset{|}{C}}}}-O)_3PS$$

These isomers and the various mixtures thereof are white liquids having a characteristic odor. Their boiling points are in the range of 140°–160°C./1 mm. The specific gravity is approximately 1.3 at 20°C. as compared with water at 4°C. They are relatively non-viscous, having a viscosity of approximately 30.1 centipoises at 30°C. They have the property of being extremely soluble in mineral oil hydrocarbons. This preferred compound contains approximately 31.5 percent carbon, 5.3 percent hydrogen, 30.8 percent chlorine, 14.0 percent oxygen, 9.1 percent phosphorus and 9.3 percent sulfur. Due to the high solubility of this preferred compound in mineral oil and to its high rate of solution therein, it can be blended readily into all types of mineral oils even at high concentration. Furthermore, the resulting mineral oil solutions remain completely homogeneous even at extremely low temperatures.

The stabilizers of the present invention are selected from compounds having the formula

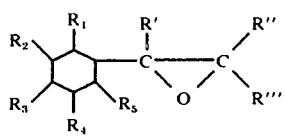 (I)

wherein $R_1$–$R_5$ and $R'$ – $R'''$ are independently selected from hydrogen and hydrocarbyl radicals selected from alkyl, cycloalkyl, alkenyl, aryl, aralkyl, and alkaryl radicals having up to about 12 carbon atoms such that the total number of carbon atoms in said compound does not exceed about 20.

Below are listed some non-limiting examples of hydrocarbyl groups which may be present in the above general formula 1 as groups $R'$ – $R'''$ and $R_1$–$R_5$. Examples of alkyl groups represented by the groups $R'$ – $R'''$ and $R_1$–$R_5$ in the above general formula are methyl, ethyl, n-propyl, isopropyl, n-butyl, isobutyl, sec-butyl, tert-butyl, n-amyl, and the various positional isomers thereof, and likewise the corresponding straight and branched chain isomers of hexyl, heptyl, octyl, nonyl, decyl, undecyl, dodecyl, and the like.

When said groups $R_1$–$R_5$ and $R'$ – $R'''$ are cycloalkyl groups, they may be cyclopropyl, cyclobutyl, cyclopentyl, cyclohexyl, cycloheptyl, cyclooctyl, cyclononyl, cyclodecyl, cycloundecyl, cyclododecyl, and the like. They may also be such cycloaliphatic groups as α-cyclopropyl-ethyl, α-cyclobutylpropyl, and similar alkyl derivatives of the higher cycloalkyls.

The groups $R_1$–$R_5$ and $R'$–$R'''$ in the above general formula may also be alkenyl groups such as ethenyl, 1-propenyl, 2-propenyl, isopropenyl, 1-butenyl, 3-butenyl, and the corresponding branched-chain isomers thereof as, for example, 1-diisobutenyl, 2-isobutenyl, 2-sec-butenyl, including 1-methylene-2-propenyl, and the various isomers of pentenyl, hexenyl, heptenyl, octenyl, nonenyl, decenyl, undecenyl, and dodecenyl, including 3,3-dimethyl-1-butenyl, 2,3-dimethyl-2-butenyl, 2,3-dimethyl-2-dimethyl-1-butenyl, 2,3-dimethyl-3-butenyl, 1-methyl-1-ethyl-2-propenyl, and the like.

When said groups $R_1$–$R_5$ and $R'$–$R'''$ are alkaryl groups, they may be 2,3-xylyl, 2,4-xylyl, 2,5-xylyl, 2,6-xylyl, 3,4-xylyl, 3,5-xylyl; o, m, and p-cumenyl, mesityl, o, m, and p-ethylphenyl, 2-methyl-1-naphthyl, 3-methyl-1-naphthyl, 4-methyl-1-naphthyl, 5-methyl-2-naphthyl, 6-methyl-3-naphthyl, 7-methyl-1-naphthyl, 8-methyl-4-naphthyl, 1-ethyl-2-naphthyl, and its various positional isomers, and the like.

Examples of aryl groups which may be present in the above general formula are phenyl, naphthyl, and the like.

When the groups $R_1$–$R_5$ and $R'$–$R'''$ are aralkyl groups, they may be benzyl, phenylethyl, 1-phenylpropyl, 2-phenylpropyl, 3-phenylpropyl, 1 and 2 isomers of phenylisopropyl, 1,2, and 3 isomers of phenylbutyl, and the like.

Such compounds suggest the use of stable, related compounds in which one or more of the groups $R_1$–$R_5$ and $R'$–$R'''$ contain a non-hydrocarbon substituent such as —Cl, —Br, —OH, —NH$_2$, and the like.

In general, the preferred stabilizers of this invention have up to about 20 carbon atoms and the styrene oxide nucleus

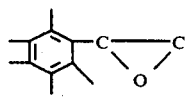

wherein the substituents appended are hydrogen, aliphatic radicals or benzenoid radicals. For purposes of this invention, benzenoid radicals are those having the benzene nucleus and are phenyl, naphthyl, substituted phenyl, and substituted naphthyl radicals. The substituted phenyl and naphthyl radicals include the alkaryl and aralkyl radicals. Of these stabilizers, those having hydrogen or aliphatic substituents are preferred. Of the aliphatic substituents, alkyl is preferred, especially those alkyl radicals of up to about 6 carbon atoms. In general, the most preferred stabilizers have no more than 2 alkyl radicals appended to the styrene oxide nucleus and these radicals have up to about 6 carbons.

In other words, the most preferred stabilizers have at least six hydrogens appended to the styrene oxide nucleus and any remaining substituents (of $R_1$–$R_5$ and $R'$–$R'''$ of Formula I) are alkyl radicals of up to about 6 carbons. Some illustrative examples of these compounds are styrene oxide, p-butylstyrene oxide, p-tetradecylstyrene oxide, α-methyl styrene oxide and α-n-butyl styrene oxide, α-β-dimethylstyrene oxide, β-n-butyl styrene oxide, β,β-di-n-butylstyrene oxide, β-methylstyrene oxide, α,β,β-triethylstyrene oxide, p-n-hexylstyrene oxide, 3,5-di-n-hexylstyrene oxide, 1,2,3,4,5-pentamethylstyrene oxide, 4-phenylstyrene oxide, p-(3,4-xylyl)styrene oxide, p-cyclohexylstyrene oxide, 2-phenylethylstyrene oxide and 3,5-di-n-butylstyrene oxide.

Styrene oxide is a most preferred stabilizer. Although one stabilizer can be used, a mixture of stabilizers can be employed if desired. Thus 2, 3, or more styrene oxide stabilizers can be added to the β-(halopropyl)-thionophosphates, preferably the tri-(β-chloropropyl)-thionophosphates. A typical stabilizing mixture is styrene oxide and α-methyl styrene oxide.

A stabilizing amount of stabilizer is employed. By stabilizing amount is meant that amount of stabilizer of formula I which is effective to stabilize the β-(halopropyl)-thionophosphates, preferably the tri-(β-chloropropyl)-thionophosphates. In other words, an effective amount of stabilizer, which amount is effective to stabilize the β-(halopropyl)-thionophosphates against deterioration, is used. The amount used can be varied and is dependent, at least to some extent, on the nature of the material being stabilized and the activity of the stabilizer. In general, the amount of stabilizer is from about 0.005 weight percent to about 10 weight percent, usually less than 10 percent and more than 0.005 percent. A preferred concentration range is from about 0.01 weight percent to about 5 weight percent, a more preferred concentration range is from about 0.05 percent to about 3 percent, most preferably from about 0.1 percent to about 2 percent.

The stabilizer and material to be stabilized can be admixed in any known manner. The mixture can be heated to facilitate solution, if desired.

Illustrating the activity of this invention, tests were conducted on a Blank, a non-stabilized tri-(β-chloropropyl)-thionophosphate specimen, and Sample 1, tri-(β-chloropropyl)-thionophosphate stabilized with 1 weight percent of styrene oxide.

After preparation and after storage at 110°F. for various intervals the total acid number was measured in accordance with ASTM test procedure D664-58.

The results were as follows:

TABLE I

| Time | Total Acid Number | |
|---|---|---|
| | Blank | Sample 1 |
| Initial | 0.23 | 0.46 |
| 6 weeks | 0.30 | 0.45 |
| 12 weeks | 1.0 | 0.4 |

It can be seen from Table I above that while the total acid number of the unstabilized blank increased over fourfold during the 12 week test period, the total acid number of the stabilized compound remained substantially unchanged during this 12 week period.

Furthermore, one or more of the aforementioned styrene oxides can be mixed with stabilizers of different types. In such mixtures, the relative amounts of stabilizers is not critical. Thus, the relative amounts are selected by such considerations as economics, degree of stabilization desired, compatibility of the admixed stabilizers with themselves and the substrate to be stabilized, and the like. In general, favorable results are obtained if the total concentration of stabilizer is from about 50 to about 100,000 ppm by weight, preferably from about 100 to about 50,000 ppm, and the proportion of the above styrene oxides in the stabilizing mixture is at least about 50 percent, i.e., at least half of the added stabilizing composition is a styrene oxide of formula I and the remainder can be a stabilizer or a mixture of stabilizers other than styrene oxides of formula I.

With such considerations in mind, mixtures of the above styrene oxides can be formulated with, for example A. Glycidyl ethers having the formula

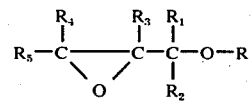

where $R_1$–$R_5$ are hydrogen or the hydrocarbyl radicals of the type discussed above, with respect to formula I, have up to about 12 carbons such that the total number of carbons does not exceed about 15;

B. Epibromohydrin, epichlorohydrin and alkylene oxides such as those within German Pat. No. 1,443,641. Of these alkylene oxides, propylene oxide is typical;

C. Compounds of the formula

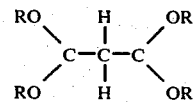

where the various Rs are hydrocarbyl groups of up to about 14 carbons of the type discussed above, with respect to formula I;

D. Orthoesters selected from compounds having the formula

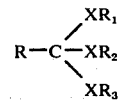

wherein X is oxygen or sulfur, R is hydrogen or an alkyl radical of up to about 4 carbon atoms, and $R_1$, $R_2$ and $R_3$ are hydrocarbyl groups selected from the class consisting of alkyl, cycloalkyl, alkenyl, aryl, and aralkyl groups having up to about 9 carbon atoms, and E. Acetylenic alcohols, such as methyl pentynol, of the formula -continued

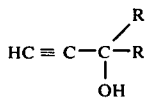

wherein R is as in formula I above.

Another embodiment of the present invention is a stabilized additive composition for hydraulic fluids comprising β-(halopropyl)-thionophosphates and a stabilizing amount of a compound of formula I. These additive fluids can be added to hydraulic fluids to improve the lubricating characteristics thereof. Thus, the additives of the present invention can be classified as lubricating additives.

The hydraulic fluids, particularly the hydraulic mineral oil, to which the stabilized β-(halopropyl)-thionophosphates are added can also contain other additives which are normally added to hydraulic oils. These include antioxidants such as the hindered phenols, an example of which is 4,4'-methylene-bis(2,6-di-tert-butylphenol), and amines, an example of which is phenyl-1-naphthylamine; corrosion inhibitors which include sodium salts of petroleum sulfuric acids, esters of naphthenic or wax oxidation acids and metal soaps of various acids; viscosity index improvers such as polylaurylmethylacrylates, polybutenes and ethylene-propylene copolymers; dispersants such as the high molecular weight (800–3000) alkyl succinimides of ethylenepolyamines, and the high molecular weight (800–3000) alkylphenol-formaldehyde-amine (e.g., N,N-dimethyl-1,3-propanediamine or tetraethylenepentamine), Mannich condensation products; foam inhibitors such as silicanes present in the dispersed phase having particles of less than 100 microns; and demulsifiers such as dimerized, unsaturated, aliphatic monocarboxylic acids.

These other additives can already be present in the hydraulic fluids, preferably the mineral oil based hydraulic fluids, to which the stabilized β-(halopropyl)-thionophosphate is added or they can be added together with said stabilized β-(halopropyl)-thionophosphate, that is, they may be included in an additive package containing the stabilized β-(halopropyl)-thionophosphate.

An example of such a useful additive concentrate is set forth below.

An additive concentrate was formulated by blending 40 parts by weight of styrene oxide stabilized tri-(β-chloropropyl)-thionophosphate, i.e., 1 part by weight of styrene oxide and 39 parts by weight of tri-(β-chloropropyl)-thionophosphate, 40 parts by weight of 2,6-di-tert-butylphenol, and 20 parts by weight of neutral barium dinonylnaphthalene sulfonate.

The primary lubrication function of a hydraulic fluid appears to be its ability to reduce friction between contacting surfaces. This can be accomplished by the base stock itself or by means of additives. However, base stock fluids can fail to give satisfactory lubrication under conditions of heavy load, high speed and high localized temperatures. Failure may be exhibited as high rate of wear, or scoring and welding of mating surfaces.

For purposes of the present invention the widely used classification of base stock fluids into two classes — petroleum or synthetic — will be adhered to. Under this classification petroleum hydraulic fluids are products which can be obtained from petroleum by normal refining procedures. These include physical separation techniques such as distillation, clay treating, dewaxing, solvent refining, and the like, and chemical treatments such as cracking, polymerization, cyclization, hydrogenation, and the like. The synthetics include those materials which are the result of chemical reactions. The term synthetic is limited to those materials which are prepared by major chemical reactions, even though the starting materials are derived from petroleum.

This classification developed naturally from the wide-spread use of petroleum-type hydraulic fluids. As synthetic fluids were introduced, it became common to refer to any non-petroleum fluid as "synthetic."

Some examples of generally recognized classes of hydraulic fluids are petroleum, phosphate esters, silicate esters, chlorinated hydrocarbons, fluorinated hydrocarbons, organic esters, silicanes, water-glycol, water-emulsion, polyalkylene glycols, polyphenyl ethers, polyphenols, hydrocarbons, silanes, and no-beta hydrogen esters.

Preferred hydraulic fluids are the petroleum derived hydraulic fluids.

Typical properties of some petroleum hydraulic fluids are set forth in Table II below.

TABLE II

| Viscosity Grade | Viscosity in SSU (100°F) | (210°F) | Viscosity Index | Flash Point (°F) | Fire Point (°F) | Pour Point (°F) | API Gravity |
| --- | --- | --- | --- | --- | --- | --- | --- |
| 150 | 140–160 | 42–44 | 90–100 | 380 | 430 | −20 to + 10 | 28–32 |
| 200 | 190–210 | 44–46 | 90–100 | 390 | 440 | − 5 to + 15 | 26–30 |
| 300 | 290–310 | 52–42 | 90–100 | 410 | 460 | + 5 to + 15 | 25–30 |
| 400 | 390–420 | 58–61 | 90–100 | 420 | 470 | + 5 to + 15 | 25–29 |
| 500 | 500–525 | 63–66 | 90–100 | 440 | 490 | + 5 to + 15 | 24–28 |
| 600 | 600–650 | 68–71 | 90–100 | 460 | 510 | + 5 to + 25 | 24–28 |
| 750 | 750–800 | 73–76 | 90–100 | 480 | 530 | + 5 to + 25 | 23–27 |
| 900 | 900–1000 | 83–86 | 90–100 | 500 | 550 | +10 to + 30 | 23–27 |

Of the petroleum hydraulic fluids mineral oil based hydraulic fluids are preferred.

The additives of the present invention, i.e., the stabilized β-(halopropyl)-thionophosphates, preferably the tri-(β-chloropropyl)-thionophosphates are incorporated into the hydraulic fluids, preferably the petroleum hydraulic fluids and more preferably mineral oil based hydraulic fluids, in an effective or sufficient amount so as to provide the required antiwear properties. By an effective amount is meant an amount of stabilized β-(halopropyl)-thionophosphate effective to impart to or enhance the antiwear properties of the fluid. A useful range is from about 0.01 to about 5 weight percent of stabilized β-(halopropyl)-thionophosphate, and a preferred range is from about 0.1 to about 3 weight percent.

Methods of incorporating the additive, i.e., the stabilized β-(halopropyl)-thionophosphates, preferably the tri-(β-chloropropyl)-thionophosphates, into the base stock fluid are well known. For example, the additive can be merely mixed into the base stock. The following will serve to illustrate the manner in which the additives are blended with the base stock fluids.

To 100 parts by weight of mineral oil base stock is added 0.2 parts by weight of styrene oxide stabilized tri-(β-chloropropyl)-thionophosphate. The mixture is stirred until thoroughly blended, resulting in a stable mineral hydraulic oil.

To 100 parts by weight of mineral oil base stock is added 0.16 parts by weight of stabilized tri-(β-chloro-n-propyl)-thionophosphate. The mixture is stirred until thoroughly blended, resulting in a stable mineral hydraulic oil.

While not being bound by any theory it is believed that the stabilized additives of the present invention, i.e., the β-(halopropyl)-thionophosphates, preferably the tri-(β-chloropropyl)-thionophosphates, function as extreme pressure and antiwear agents when added to the base stock hydraulic fluid. Thus, they impart satisfactory lubricity to the base stock under conditions of heavy load, high speed and high localized temperatures.

However, when the unstabilized β-(halopropyl)-thionophosphates of the present invention are added to hydraulic fluids it is found that under certain conditions of elevated temperature and after standing for a prolonged period of time they tend to deteriorate to a certain degree forming corrosive acids and malodorous mercaptans. As previously mentioned, these β-(halopropyl)-thionophosphates can be stabilized against deterioration by the addition of a small but effective amount of a stabilizer selected from compounds of formula I. Thus, still another embodiment of the present invention is an improved hydraulic fluid composition containing stabilized β-(halopropyl)-thionophosphates, preferably stabilized tri-(β-chloropropyl)-thionophosphates.

It is to be understood that the stabilized β-(halopropyl)-thionophosphates of the present invention can also be utilized as additives for liquid hydrocarbon fuels such as gasoline and as additives for lubricating oils.

Claims to the invention follow.

I claim:

1. A stabilized composition comprising a β-(halopropyl)-thionophosphate and an amount effective to stabilize said β-(halopropyl)-thionophosphate of a compound having the formula

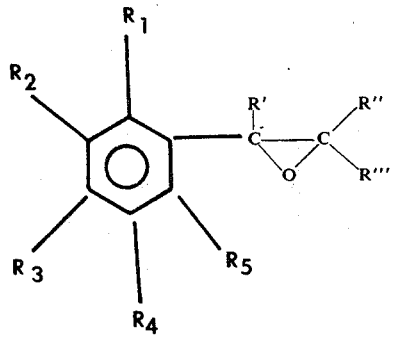

wherein $R_1$–$R_5$ and $R'$ – $R'''$ are independently selected from hydrogen and hydrocarbyl radicals.

2. The composition of claim 1 wherein said β-(halopropyl)-thionophosphate is tri-(β-chloropropyl)-thionophosphate.

3. The composition of claim 2 wherein said compound has up to about 20 carbon atoms.

4. The composition of claim 3 wherein said hydrocarbyl radicals are alkyl radicals.

5. The composition of claim 4 wherein said alkyl radicals have from 1–6 carbon atoms.

6. The composition of claim 5 wherein said compound is styrene oxide.

7. The composition of claim 2 wherein said tri-(β-halopropyl)-thionophosphate is tri-(β-chloropropyl)-thionophosphate.

8. The composition of claim 7 wherein said tri-(β-halopropyl)-thionophosphate is tri-(β-chloro-n-propyl)-thionophosphate.

9. The composition of claim 7 wherein said tri-(β-halopropyl)-thionophosphate is tri-(β-chloroisopropyl)-thionophosphate.

10. The composition of claim 5 wherein said composition comprises from about 100 to about 50,000 ppm by weight of said compound.

11. An improved petroleum hydraulic fluid containing an amount effective to enhance the antiwear properties of said fluids of β-(halopropyl)-thionophosphate and an amount effective to stabilize said β-(halopropyl)-thionophosphate of a compound having the formula

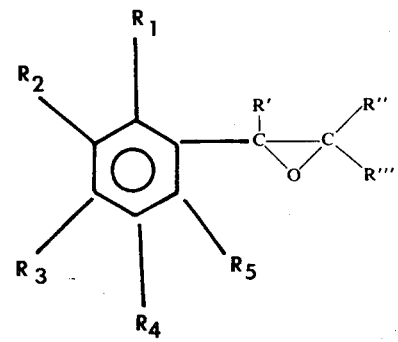

wherein $R_1$–$R_5$ and $R'$ – $R'''$ are independently selected from hydrogen and hydrocarbyl radicals.

12. The composition of claim 11 wherein said β-(halopropyl)-thionophosphate is tri-(β-chloropropyl)-thionophosphate.

13. The improved petroleum hydraulic fluid of claim 12 wherein said fluid contains from about 100 ppm by weight to about 50,000 ppm by weight of said β-(halopropyl)-thionophosphate and from about 0.05 ppm by weight to about 2,500 ppm of said compound.

14. An improved hydraulic mineral oil containing an amount effective to enhance the antiwear properties of said oil of β-(halopropyl)-thionophosphate and an amount effective to stabilize said β-(halopropyl)-thionophosphate of a compound having the formula

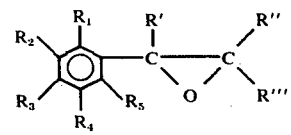

wherein $R_1$–$R_5$ and $R'$ – $R'''$ are independently selected from hydrogen and hydrocarbyl radicals.

15. The improved hydraulic mineral oil of claim 14 wherein said oil contains from about 1000 ppm to about 50,000 ppm by weight of said β-(halopropyl)-thionophosphate and from about 0.05 to about 2,500 ppm of said compound.

* * * * *